US010349994B1

United States Patent
Elgafy et al.

(10) Patent No.: US 10,349,994 B1
(45) Date of Patent: Jul. 16, 2019

(54) BONE GRAFT MATERIAL MIXING AND DELIVERY DEVICE

(71) Applicant: The University of Toledo, Toledo, OH (US)

(72) Inventors: Hossein Elgafy, Toledo, OH (US); Anand K. Agarwal, Ottawa Hills, OH (US); Vijay K. Goel, Holland, OH (US); Narjes Momeni Shahraki, Toledo, OH (US); Amey V. Kelkar, Toledo, OH (US)

(73) Assignee: The University of Toledo, Toledo, OH (US)

( * ) Notice: Subject to any disclaimer, the term of this patent is extended or adjusted under 35 U.S.C. 154(b) by 665 days.

(21) Appl. No.: 14/674,502

(22) Filed: Mar. 31, 2015

Related U.S. Application Data

(60) Provisional application No. 61/972,864, filed on Mar. 31, 2014.

(51) Int. Cl.
*A61B 17/88* (2006.01)
*A61F 2/46* (2006.01)

(52) U.S. Cl.
CPC .. *A61B 17/8833* (2013.01); *A61B 2017/8838* (2013.01); *A61F 2/4601* (2013.01)

(58) Field of Classification Search
CPC ........ A61F 2/46; A61F 2/4601; A61F 2/2846; A61F 2002/4602; A61F 2002/2835; A61B 17/8802; A61B 17/8805; A61B 2017/8838; A61B 50/20; A61B 50/33; A61B 2050/005; A61B 2050/0051; A61B 2050/0056
See application file for complete search history.

(56) References Cited

U.S. PATENT DOCUMENTS

| 3,789,852 | A * | 2/1974 | Kim .................. | A61B 17/3439 604/104 |
| 4,800,875 | A * | 1/1989 | Ray ....................... | A61F 2/4601 141/331 |
| 7,226,451 | B2 * | 6/2007 | Shluzas .............. | A61B 1/00149 600/219 |
| 7,491,168 | B2 * | 2/2009 | Raymond .............. | A61B 17/02 600/231 |
| 8,343,048 | B2 * | 1/2013 | Warren, Jr. ............ | A61B 17/02 600/233 |

* cited by examiner

*Primary Examiner* — Kevin T Truong
*Assistant Examiner* — Tracy L Kamikawa
(74) *Attorney, Agent, or Firm* — MacMillan, Sobanski & Todd, LLC

(57) ABSTRACT

Described herein are bone graft material (BGM) delivery devices having a tray configured to provide a mixing and/or holding area for BGM to substantially prevent BGM from inadvertently being delivered to an unacceptable surgical site.

12 Claims, 11 Drawing Sheets

BONE GRAFT MATERIAL MIXING AND DELIVERY DEVICE

CROSS-REFERENCE TO RELATED APPLICATIONS AND STATEMENT REGARDING FEDERALLY SPONSORED RESEARCH

This application claims the priority to U.S. Provisional Application No. 61/972,864 filed Mar. 31, 2014, the entire disclosure of which is expressly incorporated herein by reference. This invention was not made with any government support, and the government has not rights in the invention.

BACKGROUND OF THE INVENTION

There is a need for a device which allows for the efficient mixing and delivering of bone graft materials by a practitioner at a point in time before or during a surgical procedure, and at a place adjacent to a surgical site.

SUMMARY OF THE INVENTION

Described herein is a bone graft material (BGM) delivery device for use by a practitioner in delivering BGM at a surgical site in a patient. The BGM delivery device is particularly useful for being positioned adjacent intervertebral joints in a human spine during fusion surgery. In a particular embodiment, the BGM delivery device is useful in surgeries which achieve a desired fusion between the transverse processes of the human spine.

The various embodiments of the BGM delivery device provides the practitioner with a desired flexibility in the manner in which BGM is delivered to one or more motion segments of the human spine at once.

Thus, there is a need to improve the efficacy and consistency of delivery systems by mixing the constituents of the BGMs (for example, BGMs include bone materials, synthetic materials and/or other bioactive agents) to be positioned, and then delivered in a timely manner. It is to be understood that the types of BGMs that can be delivered using the embodiments described herein are known to those skilled in the art. Non-limiting examples of BGMs include bioactive agents or bioactive compounds such as a compound or entity that alters, inhibits, activates, or otherwise affects biological or chemical events. Bone, as used herein, refers to bone that is cortical, cancellous or cortico-cancellous of allogenic, autogenous, transgenic or xenogenic origin.

More specifically, the assembled devices of the present disclosure allow various angular approaches to a targeted area. The BGM delivery devices enables repeatable, controlled delivery of BGMs to a target area in the patient.

The BGM delivery device can be positioned against an implant or a portion of the bone to substantially prevent any BGMs from falling into the spinal canal, or other undesirable part of the surgical site.

The BGM delivery device provides a readily accessible holding area for allowing the practitioner to mix the BGMs immediately before use. The BRM delivery device also allows the practitioner, after mixing of the BGMs to fold such materials if desired, and then deliver the mixed/folded BGMs into the patient without requiring the practitioner to need to transfer the BGMs into various different containers.

The BGM delivery devices described herein are configured such that the BGM delivery device is positionable in a generally stabilized and lateral alignment with respect to the surgical area.

Various aspects of this invention will become apparent to those skilled in the art from the following detailed description of the preferred embodiments, when read in light of the accompanying drawings.

DETAILED DESCRIPTION OF THE PREFERRED EMBODIMENTS

Figures 1, 2:
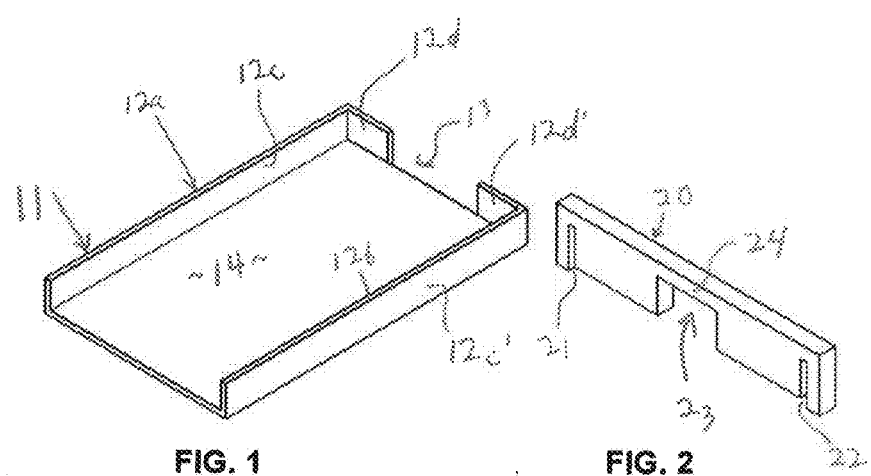
FIG. 1 is a perspective view of a tray of a first embodiment of a BGM delivery device.
FIG. 2 is a perspective view of a width-adjustment member useful with the tray of FIG. 1 in a first embodiment of a bone graft material (BGM) delivery device.

For the purposes of this specification and appended claims, unless otherwise indicated, all numbers expressing quantities of ingredients, percentages or proportions of materials, reaction conditions, and other numerical values used in the specification and claims, are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

The terms "upper", "lower", "top", "bottom", "side", "proximal", "distal" and so forth have been used herein merely for convenience to describe the present invention and its parts as oriented in the drawings. It is to be understood, however, that these terms are in no way limiting to the disclosure since the delivery systems described herein may obviously be disposed in different orientations when in use.

Notwithstanding the numerical ranges and parameters set forth herein, the broad scope of the invention are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all subranges subsumed therein. For example, a range of "1 to 10" includes any and all subranges between (and including) the minimum value of 1 and the maximum value of 10, that is, any and all subranges having a minimum value of equal to or greater than 1 and a maximum value of equal to or less than 10, e.g., 5.5 to 10.

Reference will now be made in detail to certain embodiments of the invention, examples of which are illustrated in the accompanying drawings. While the invention will be described in conjunction with the illustrated embodiments, it will be understood that they are not intended to limit the invention to those embodiments. On the contrary, the invention is intended to cover all alternatives, modifications, and equivalents that may be included within the invention as defined by the appended claims.

Figure 3:
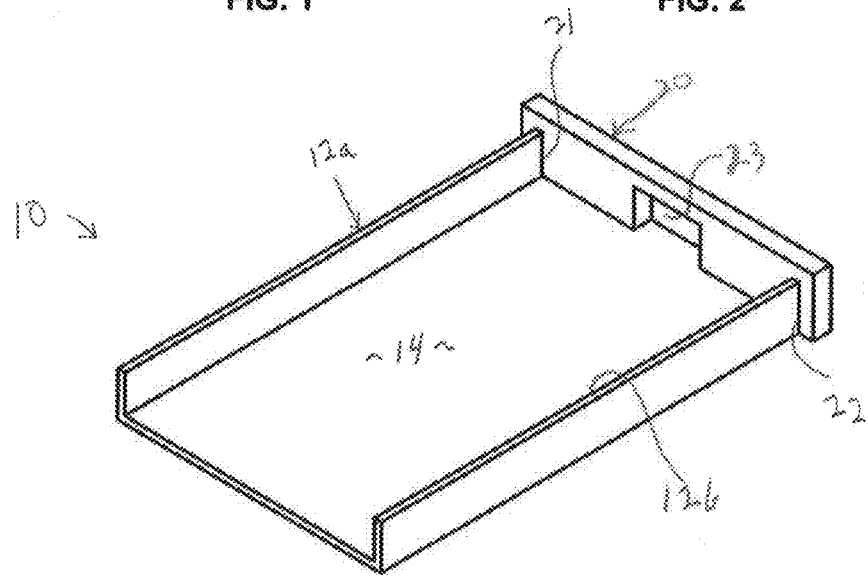
FIG. 3 is a perspective view showing the tray of FIG. 1 and the width-adjustment member of FIG. 2 assembled into a first embodiment of a BGM delivery device.

FIGS. 1 through 3 illustrate a first embodiment of a BGM delivery device 10 having a tray 11 and a width-adjustment member 20 which can be used together as an assembly. As best shown in FIG. 1, the tray 11 has a generally U-shape, as defined by two opposing L-shaped arms 12a and 12b, and a platform 14 that spans between the opposing arms 12a and 12b.

The opposing arms 12a, 12b define an opening 13 that is adjacent to one end of the platform 14. It is to be understood that while the embodiment of the platform 14 shown has a substantially planar surface, other embodiments of the platform 14 can have, for example, curved, frustoconical or other useful configurations. The platform 14 can serve as a mixing and/or holding area for the BGMs.

Each arm 12a, 12b has longitudinally extending portions 12c, 12c' (i.e., the long portion of an L-shape) that extend along a length of the platform 14 at an angle with respect to a plane defined by the platform 14. Each arm 12a, 12b has transverse extending portions 12d, 12d' (i.e., the short portion of an L-shape) that extend along a length of the platform 14 at an angle with respect to a plane defined by the platform 14. In the embodiment shown, longitudinally extending portions 12c, 12c' are at a right angle with respect to the transverse extending portions 12d, 12d'; however, it is to be understood that either or both of the angles defined by portions 12c and 12d and/or 12c' and 12d' can be other than right angles. For example, the portions 12c/12d and/or 12c'/12d' can form a V-shape, that aids in allowing the practitioner to funnel the BGM into the surgical site.

In one embodiment, the tray opening 13 can, for example, be about 38 mm in width. Referring now to FIG. 2, the width-adjustment member 20 can also have a generally U-shape, as defined by two opposing slots 21 and 22 connected together by a central portion 24 such that the central portion defines an opening 23. The two slots 21 and 22 of the width-adjustment member 20 can be slidingly assembled onto the opposing arms 12a and 12b of the tray 11, as shown in FIG. 3. When so assembled, the tray 11 and the width-adjustment member 20 cooperate such that the tray opening 13 is reduced by the width defined by the opening 23 in the width-adjustment member 20. In one embodiment, the width of the opening 24 can by about 19 mm.

During use in, for example, a posterolateral spinal fusion surgery, the BGM delivery device is positioned such that the tray opening 13 (or the width-adjustment member opening 23—if the width-adjustment member 20 is in position on the tray 11), is held by the practitioner at an angle with respect to an implant device, such as, for example a metal rod connecting two or more pedicle screws. The practitioner can urge the BGMs that are on the platform 14 through either the opening 13 (or opening 23) a controlled and precise manner to an exact location.

Figure 4:
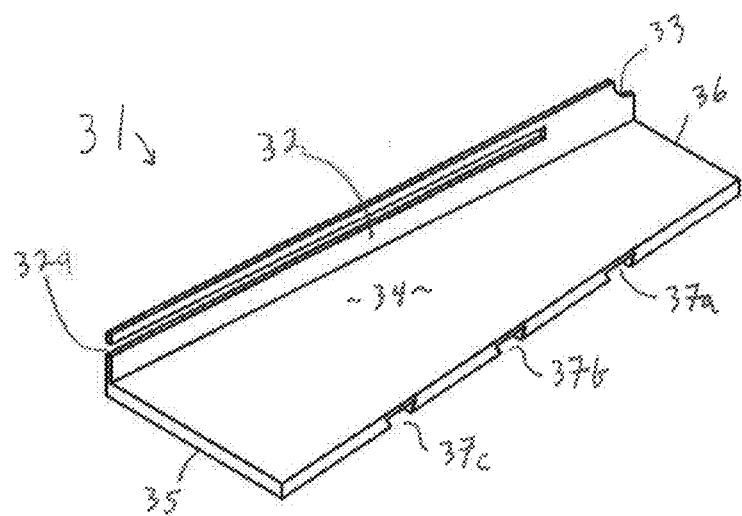
FIG. 4 is a perspective view of a tray that is part of a second embodiment of a BGM delivery device.
Figure 5:
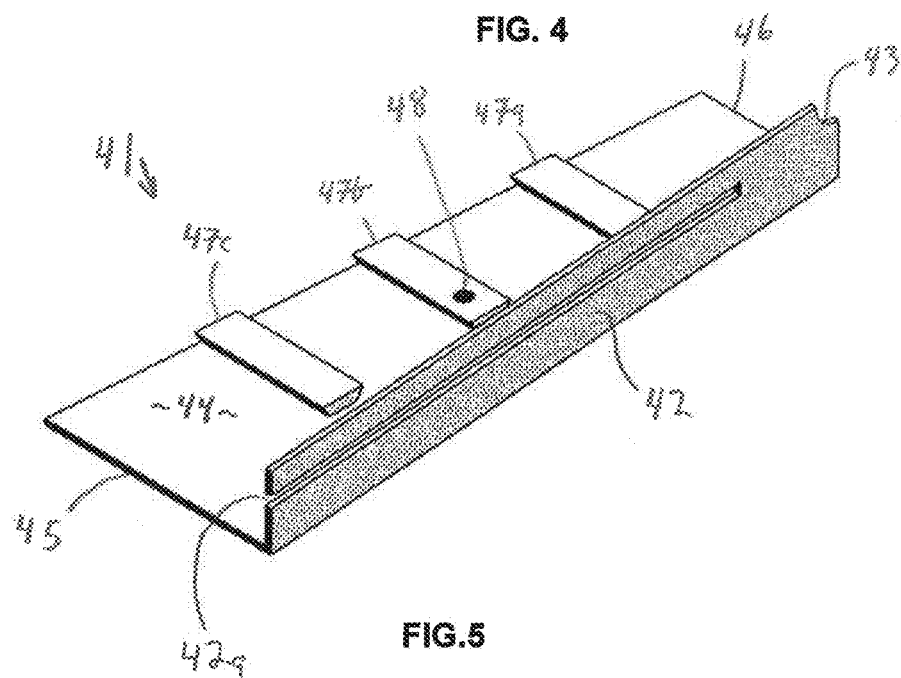
FIG. 5 is a perspective view of a width-adjustment member that is useful with the tray of FIG. 4, that forms part of the second embodiment of a BGM delivery device.
Figure 6:
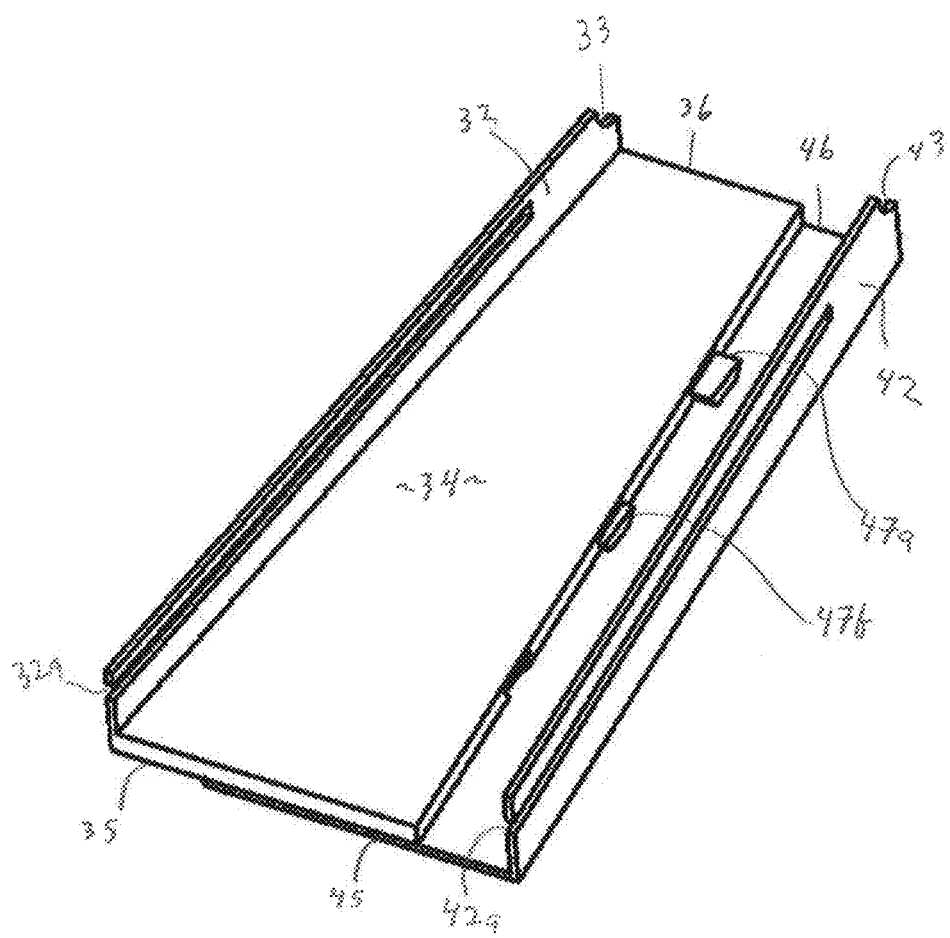
FIG. 6 is a perspective view showing the tray of FIG. 4 and the width-adjustment member of FIG. 5 assembled into a second embodiment of a BGM delivery device.

FIGS. 4 through 6 illustrate a second embodiment of a BGM delivery device having a tray 31 and a width-adjustment member 41 which can be used together as an assembly. As shown in FIG. 4, the tray 31 has a generally L-shape, as defined by a platform 34 and an arm 32. The platform 34 has a trapezoidal or tapering design, such that a first end 35 has a larger width (for example, about 41.5 mm) and a second end 36 has a smaller width (for example, about 25.5 mm). It is to be understood that while the embodiment of the platform 34 shown has a substantially planar surface, other embodiments of the platform 34 can have, for example, curved, frustoconical or other useful configurations.

The arm 32 in the tray 31 has a slot 32a provided therein that extends along its length. The arm 32 includes a curved cut 33 that is adjacent the second, smaller end 36 of the platform 34. The curved cut 33 is provided at a top corner of the arm 32. The bottom surface of the tray 31 has one or more trapezoidal shaped slots—here shown as 37a, 37b, 37c. It is to be understood, that in other embodiments, the tray 31 can have fewer or greater numbers of slots 37; and that, in certain embodiments, the slots can have a different configuration than trapezoidal. In the embodiment shown, the slots 37a, 37b, 37c are aligned in generally in a parallel manner with respect to a line defined either by the first end 35 or the second end 36 of the platform 34.

The width-adjustment member 41, as shown in FIG. 5, is similar in shape and dimensions to the tray 31. The width-adjustment member 41 includes a base 44 and an arm 42 having a slot 42*a* provided therein that extends along its length and a curved cut 43 provided therein at its top corner. The base 44 of the width-adjustment member 41 has a tapering design, such that a first end 45 has a larger width than a second end 46. The top surface of the base 44 of the width-adjustment member 41 has three trapezoidal shaped protrusion 47*a*, 47*b*, 47*c* provided therein. It is to be understood, that in other embodiments, the width-adjustment member 41 can have fewer or greater numbers of protrusions 47, and that the protrusions can have a shape other than trapezoidal. In the embodiment shown, the protrusions 47*a*, 47*b*, 47*c* are aligned in generally in a parallel manner with respect to a line defined either by the first end 45 or the second end 46 of the width-adjustment member 41.

Also, in certain embodiments, the top surface of the width-adjustment member 41 can have a threaded hole 48 provided therein, the diameter of which may, for example, be about 2.54 mm, for receiving a suitable retaining member, such as, for example, a screw, pin, bolt, and the like.

When the tray 31 and the width-adjustment member 41 are put together as an assembly (as shown in FIG. 6), the protrusions 47*a*, 47*b*, 47*c* on the width-adjustment member 41 slide into and are received within the slots 37*a*, 37*b*, 37*c*, respectively, provided on the bottom of the tray 31. Using this sliding mechanism involving the slots 37*a*, 37, 37*c* and the protrusions 47*a*, 47*b*, 47*c*, an opening that is to be proximal to the patient is defined by the distance between the arm 32 of the tray 31 and the arm 42 of the width-adjustment member 41. In certain embodiments, such distance can be varied, such as, for example, from about 25.5 mm to about 50.0 mm. The width of the opening (as defined by the smaller, second end 36) of the tray 31 can be locked as per demand by inserting a threaded screw (not shown) having, for example, a length of about 5 mm and a diameter of about 3 mm into the threaded hole 48 and tightening it.

Also, during posterolateral spinal fusion surgery, for example, the tray 31 and the width-adjustment member 41 can be restingly held at a desired angle with respect to the patient and/or the implant. This can be achieved by allowing the practitioner to position, and rest, the curved notches 33 and 43 against an outer curvature of the metal rods connecting the pedicle screws of the implant.

Figures 7, 8:
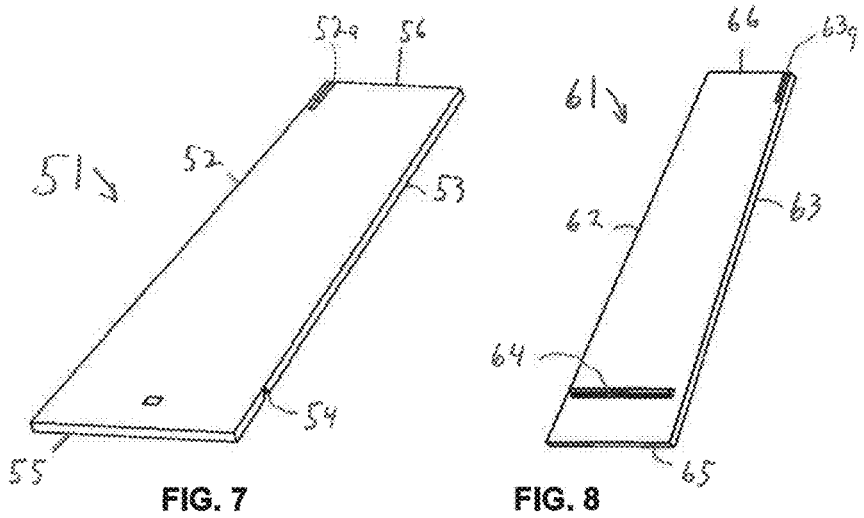
FIG. 7 is a perspective view of an upper lid assembly useful with the BGM delivery device shown in FIG. 6.
FIG. 8 is a perspective view of a lower lid assembly useful with the BGM delivery device shown in FIG. 6.

Referring now to FIGS. 7-10, if desired, a lid assembly of adjustable width can be used in conjunction with the second embodiment shown in FIG. 6. The lid assembly can include an upper lid assembly 51, as shown in FIG. 7, and a lower lid assembly 61, as shown in FIG. 8. The upper lid assembly 51 has a tapering design, such that a first end 55 has a larger width than a second end 56. The upper lid assembly 51 has opposing first and second edges 52, 53, respectively. The first edge 52 defines a slot 52*a* which extends along the length of the first edge 52 from the smaller width second end 56. The bottom surface of the upper lid assembly 51 has an inverted recess 54 (such as, for example, the t-shaped recess shown in FIG. 7). Referring now to FIG. 8, the lower lid assembly 61 is similar in shape to the upper lid assembly 51, and also has a tapering design, such that a first end 65 has a larger width than a second end 66. The lower lid assembly 61 has opposing first and second edges 62, 63, respectively. The second edge 63 defines a slot 63*a* which extends along the length of the second edge 63 from the smaller width second end 66. The lower lid assembly 61 has a protrusion 64 an upper surface thereof. The protrusion 64 can have a complementary shape with respect to the recess in the upper lid assembly 52; for example, the protrusion 64 can have an inverted T-shape.

Figure 9:
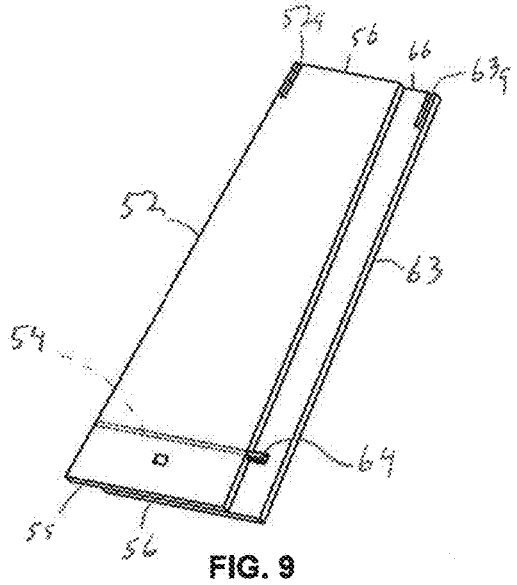
FIG. 9 is a perspective view, partially in phantom, of the assembled upper lid assembly of FIG. 7 and the lower lid assembly of FIG. 8.
Figure 10:
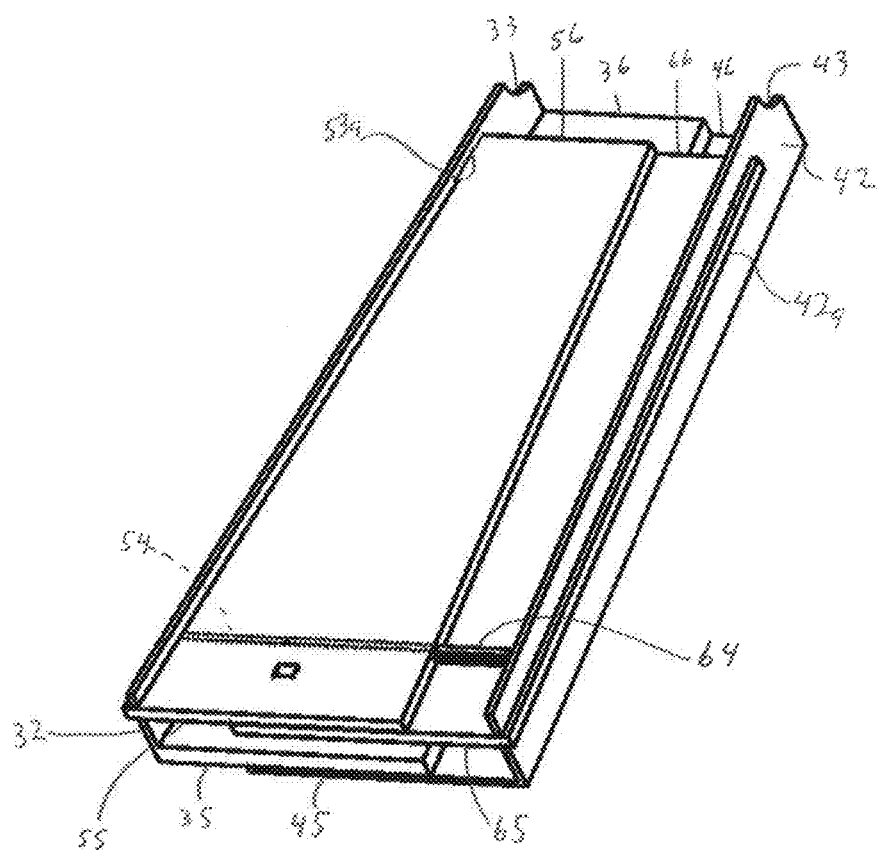
FIG. 10 is a perspective view, partially in phantom, showing the assembly upper lid assembly and the lower lid assembly of FIG. 9, assembled with the BGM delivery device of FIG. 6.

When used in conjunction with the second embodiment of the BGM delivery device, as shown in FIG. 10, the slot 52*a* of the upper lid assembly 51 slidingly mates with the slot 32*a* in the tray 31. Also, the slot 63*a* in the lower lid assembly 61 slidingly mates with the slot 42*a* in the width-adjustment member 41. The protrusion 64 on lower lid assembly 61 fits into the recess 54 on upper lid assembly 51, and forms a rail-like mechanism that can be used to adjust the width of the lid assembly, as best shown in FIG. 9.

During use of the embodiment shown in FIG. 10, the practitioner can have a first BGM held on the platform 34, while also having a second BGM held of the top surface of the upper lid assembly 51. The upper/lower lid assembly 51/61 can be in a first position; where the first position has the second narrower ends 56/66 that are slidingly positioned at a distance from the second narrower ends 35, 45 of the platform 31 and width-adjustment member 41, respectively. When in this first position, the practitioner can mix/hold/delivery the first BGM being held on the platform 34. Thereafter, without any need for repositioning of the delivery device, the practitioner can slide the assembled lid assembly 51/61 holding the second material in a direction towards the narrow second ends 36, 46 of the platform 31, width-adjustment member 41, respectively.

Alternatively, the practitioner can mix/hold the BGM on the platform 34; then, slide the assembled lid assembly 51/61 over the mixed material to protect the mixed material until such time that the practitioner is able to deliver the material at an appropriate time and place into the patient.

Figures 11, 12:
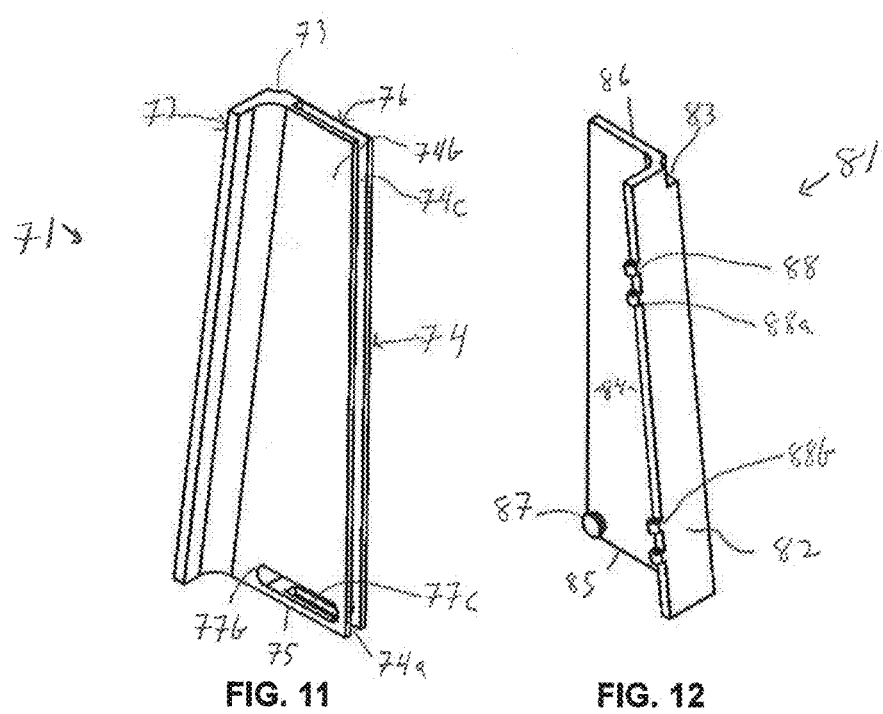
FIG. 11 is a perspective view of a tray that is part of a third embodiment of a BGM delivery device.
FIG. 12 is a perspective view of a width-adjustment member useful with the tray of FIG. 11, that forms the third embodiment of a BGM delivery device.

FIGS. 11 through 15 illustrate a third embodiment of a BGM delivery device having a tray 71 and a width-adjustment member 81 which can be used together as an assembly. As shown in FIG. 11, the tray 71 has a generally L-shape, as defined by a platform 74 and an arm 72.

The platform 74 has a tapering design, such that a first end 75 has a larger width than an opposing second end 76. The platform 74 has a slot 74*a* provided therein that extends along its length from the first end 75 to the second end 76. The platform 74 can thus be generally described as having an upper surface 74*b* and a lower surface 74*c*. Further, the platform 74 has one or more slots—here shown as 77*b* and 77*c* (for example, 30 mm wide) which extend through the upper and lower surfaces 74*b*, 74*c*, respectively, of the platform 74. It is to be understood, that in other embodiments, the platform 74 can have fewer or greater numbers of slots 77; for example, the platform 74 can have only a slot 77*c* that is in the lower surface 74*c*. In the embodiment shown, the slot 77*b*, 77*c* are aligned in generally in a parallel manner with respect to a line defined either by the first end 75 of the platform 74. It is to be understood that while the embodiment of the platform 71 shown has a substantially planar surface, other embodiments of the platform 71 can have, for example, curved, frustoconical or other useful configurations.

In certain embodiments, the arm 72 can have a cut 73 that is adjacent the second, smaller end 76 of the platform 74. The cut 73 is provided at a bottom corner of the arm 72.

The width-adjustment member 81, as shown in FIG. 12, is similar in shape and dimensions to the tray 71. The width-adjustment member 81 includes a base 84 and an arm 82; in certain embodiments, the arm 82 can have and a cut 83 provided therein at its bottom corner. The base 84 of the width-adjustment member 81 has a tapering design, such that a first end 85 has a larger width than a second end 86. The top surface of the base 84 of width-adjustment member 81 has one or more shaped protrusion 87 provided therein. It is to be understood, that in other embodiments, the width-adjustment member 81 can have a greater numbers of protrusions 87. In the embodiment shown, the protrusion 87 is aligned in generally in a perpendicular manner with respect to the slots 77*a*, 77*b* in the platform 74.

Figure 13:
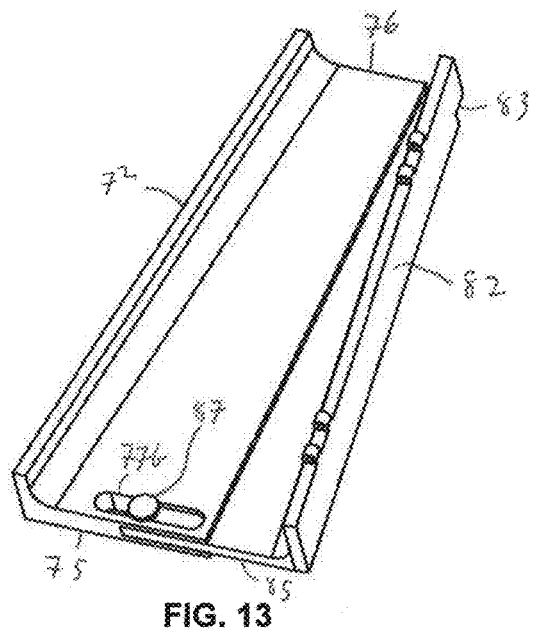
FIG. 13 is a perspective view showing the tray of FIG. 11 and the width-adjustment member of FIG. 12 assembled into the third embodiment a BGM delivery device.

When the tray 71 and the width-adjustment member 81 are put together as an assembly (as shown in FIG. 13), the protrusion 87 on the width-adjustment member 81 slides into and is received within the slots 77*b*, 77*c*, respectively, provided on the platform 74. Using this sliding mechanism involving the slots 77*b*, 77*c* and the protrusion 87, an opening that is to be proximal to the patient is defined by the distance between the arm 72 of the tray 71 and the arm 82 of the width-adjustment member 81. In certain embodiments, such distance can be varied, such as, for example, from about 25.5 mm to about 50.0 mm. In certain embodiments, the tray 71 and width-adjustment member 81 can be locked into a non-movable position, by having the protrusion 87 be configured to be capable of being tightened against the platform 74.

When put together as an assembly, the base 84 of width-adjustment member 81 slides into the slot 74*a* created in the platform 74 of the tray 71. During posterolateral spinal fusion surgery, the assembly can be held at an angle with the horizontal plane, with the cuts 73 and 83 resting against the outer curvature of the metal rods connecting the pedicle screws.

Further referring to the width-adjustment member 81, the arm 82 can define one or more hollow cylindrical shaped extrusions 88 configured for receiving a pin-like member. That is, in the embodiment shown in FIGS. 12-13, the arm 83 of the width-adjustment member 81 has rectangular cuts 88*a* and 88*b* near its top edge that are in spaced apart relationship, such that the protrusions 88 form a knuckle-like feature of a hinge.

Figure 14:
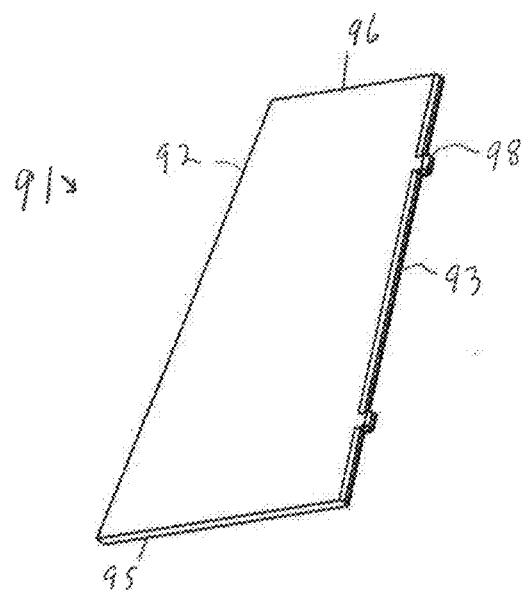
FIG. 14 is a perspective view of a lid assembly useful with the BGM delivery device shown in FIG. 13.
Figure 15:
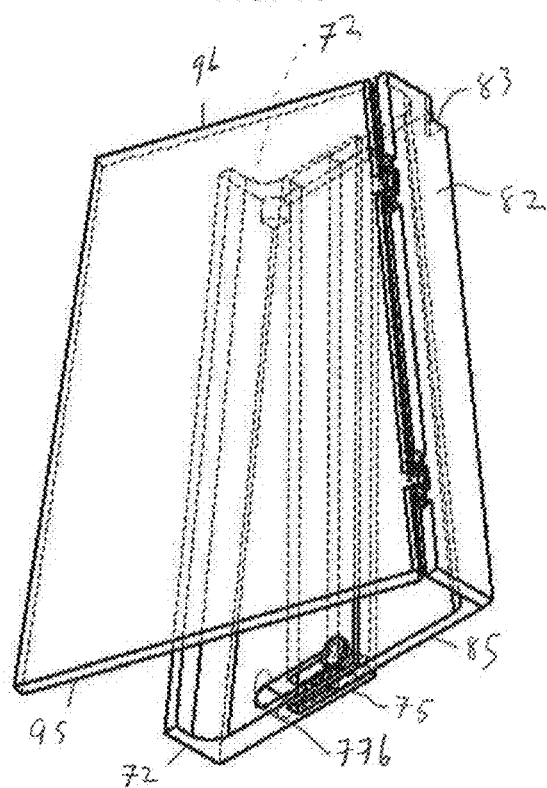
FIG. 15 is a perspective view, partially in phantom, showing the assembled BGM delivery device of FIG. 13 with the lid assembly of FIG. 14.

Referring now to FIGS. 14-15, if desired, a lid assembly 91 can be used in conjunction with the third embodiment shown in FIG. 13. The lid assembly 91 has a tapering design, such that a first end 95 has a larger width than a second end 96. The lid assembly 91 has opposing first and second edges 92, 93, respectively. The second edge 93 defines one or more hollow cylindrical shaped extrusions 98 configured for receiving a pin-like member. That is, in the embodiment shown in FIGS. 12-13, the lid assembly 91 has rectangular cuts 98*a* and 98*b* near its second edge 93 that are in spaced apart relationship, such that the protrusions 98*a*, 98*b* form knuckle-like features of a hinge. That is, the protrusions 98*a*, 98*b*, are sized and shaped to be positioned adjacent to the protrusions 88 on the arm 82 of the width-adjustment member 81 to form hinge joints that allow for opening and closing of the lid assembly 91, as shown in FIG. 15.

When used in conjunction with the third embodiment of the BGM delivery device, as shown in FIG. 15, the upper lid assembly 91 pivotably mates with the arm 82 of the width-adjustment member 81.

During use of the embodiment shown in FIG. 15, the practitioner can mix/hold the BGM on the platform 74; then, pivotably rotate the assembled lid assembly 91 over the mixed material to protect the mixed material until such time that the practitioner is able to deliver the material at an appropriate time and place into the patient.

Figure 16:
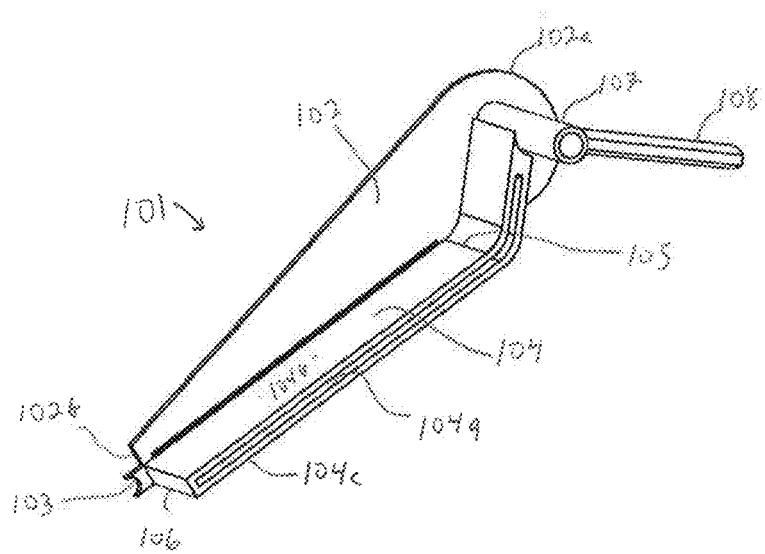
FIG. 16 is a perspective view of a tray of a fourth embodiment of a BGM delivery device.

FIGS. 16 through 19 illustrate a fourth embodiment of a BGM delivery device having a tray 101 and a width-adjustment member 111 which can be used together as an assembly. As shown in FIG. 16, the tray 101 has a generally L-shape, as defined by a platform 104 and an arm 102.

The platform 104 has can either have a generally rectangular shape, or in other embodiments, the platform 104 can have a tapering design, such that a first end 105 has a larger width than an opposing second end 106. The platform 104 has a slot 104*a* provided therein that extends along its length from the first end 105 to the second end 106. The platform 104 can thus be generally described as having an upper surface 104*b* and a lower surface 104*c*. In the embodiment shown, the slot 104*a* is closed at the end adjacent to the second, smaller end 106 of the platform 104, and the slot 104*a* (which may be 30 mm in length, for example) is generally continuously extends along a length of the platform 104 between the upper and lower surfaces 104*b*, 104*c*, respectively, of the platform 104. It is to be understood, that in other embodiments, the platform 104 can have fewer or greater numbers of slots 104; for example, the platform 104 can have a series of shorter slot that extend for limited distances along the length of the platform 104. Further, the first end 105 can be configured to have a first end 105 that extends upwardly from a plane defined by the platform 104. In the embodiment shown in in FIGS. 16 and 18, the first end 105 has a curved shape. Also, it is to be understood that while the embodiment of the platform 104 shown has a substantially planar surface, other embodiments of the platform 104 can have, for example, curved, frustoconical or other useful configurations.

Referring again to FIG. 16, the arm 102 of the tray 101 can have a cut 103 that is adjacent the second, smaller end 106 of the platform 104. The cut 103 can extend beyond the second end 106 of the platform 104. Also, as in the embodiment shown in FIG. 16, the arm 102 can have a shape that is tapering in height; for example, the arm 102 can have a first end 102*a* that is adjacent to the first end 105 of the platform 104. The first end 102*a* of the arm 102 can have a first height that is greater than a second end 102*b* of the arm 102. In the embodiment shown in FIG. 16, the second end 102*b* of the arm 102 is adjacent to, and co-terminus with, the second end 106 of the platform 104.

The first end 102*a* of the arm 102 can include an inwardly member 107; for example, the inwardly extending member 107 can, for example, be a hollow cylindrical extrusion (having an inner diameter of, for example, 10 mm). In certain embodiments, the inwardly extending member 107 can include a handle 108 that extends in a radial or perpendicular manner from an axis defined by the inwardly extending member 107.

Figure 17:
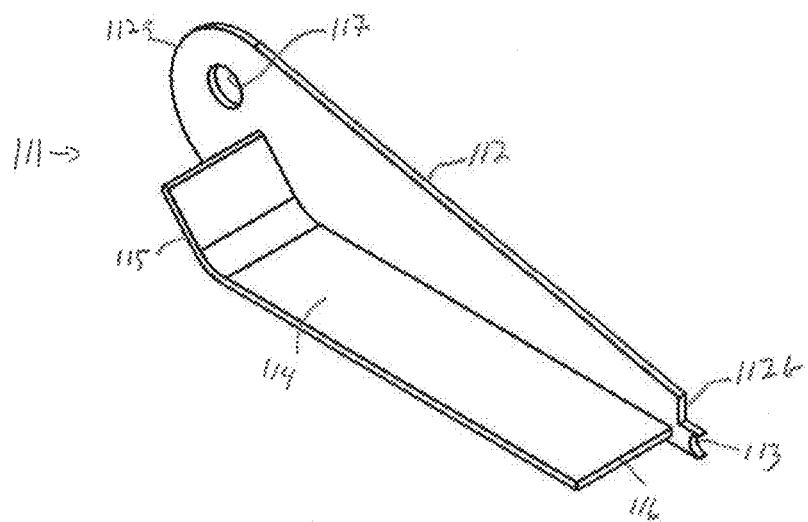
FIG. 17 is a perspective view of a width-adjustment member useful with the tray of FIG. 17, that forms the fourth embodiment of the BGM delivery device.

Referring now to FIG. 17, the width-adjustment member 111, can have a generally similar in shape and dimensions to the tray 101. The width-adjustment member 111 can either have a generally rectangular shape; or, in other embodiments, the width-adjustment member 111 has a tapering design, such that a first end 115 has a larger width than a second end 116.

The width-adjustment member 111 includes a base 114 and an arm 112. Also, as in the embodiment shown in FIG. 17, the arm 112 can have a shape that is tapering in height; for example, the arm 112 can have a first end 112*a* that is adjacent to the first end 115 of the base 114. The first end 102*a* of the arm 102 can have a first height that is greater than a second end 102*b* of the arm 102. In the embodiment shown in FIG. 17, the second end 112*b* of the arm 112 is adjacent to, and co-terminus with, the second end 116 of the base 114. Also, in certain embodiments, the arm 112 can have a cut 113 that is adjacent the second end 116 of the arm 112. The cut 113 can extend beyond the second end 116 of the arm 112.

The first end 112*a* of the arm 112 can include at least one opening 117 (for example, a circular hole of 10 mm diameter) that is configured to accept a distal end of the inwardly extending member 107 on the arm 102 of the platform 101.

Figure 18:
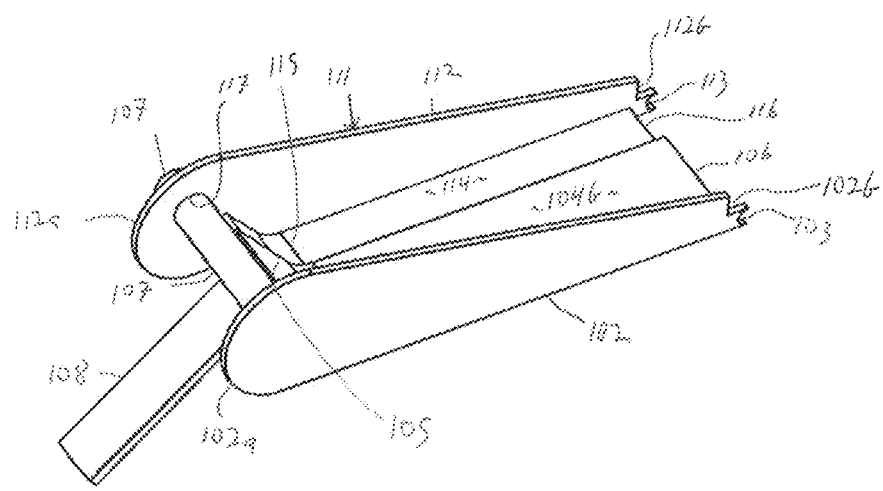
FIG. 18 is a perspective view showing the assembled tray of FIG. 16 and the width-adjustment member of FIG. 17, assembled into the fourth embodiment of the BGM delivery device.

When the tray 101 and the width-adjustment member 111 are put together as an assembly (as shown in FIG. 18), a distal end of the inwardly extending member 107 on the tray 101 slides into and is received within the opening 117 on the arm 112 of the width-adjustment member 112. Using this sliding mechanism involving the inwardly extending member 107 and the opening 117, an opening that is to be proximal to the patient is defined by the distance between the arm 102 of the tray 101 and the arm 112 of the width-adjustment member 111. In certain embodiments, such distance can be varied, such as, for example, from about 25.5 mm to about 50.0 mm. In certain embodiments, the tray 101 and width-adjustment member 101 can be locked into a non-movable position.

When put together as an assembly, the base 114 of the width-adjustment member 101 slides into the slot 104a created in the platform 104 of the tray 101. During posterolateral spinal fusion surgery, such assembly can be held at an angle with the horizontal plane, with the cuts 103 and 113 resting against the outer curvature of the metal rods connecting the pedicle screws.

Figure 19:
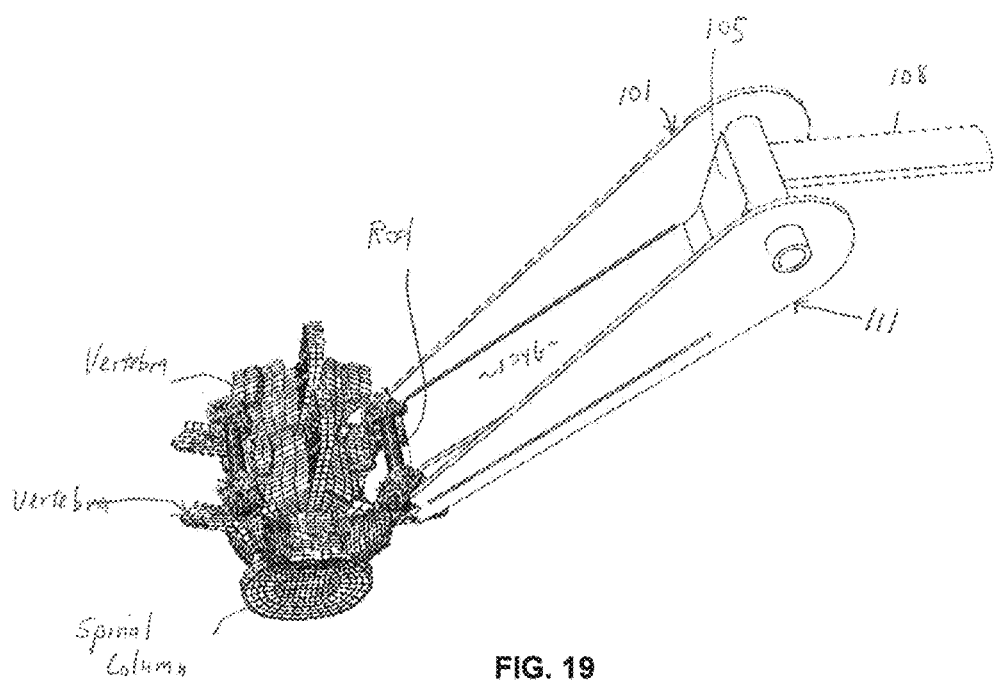
FIG. 19 is a perspective view of the assembled BGM delivery device of FIG. 19, in phantom, shown in use adjacent a spinal implant having a rod positioned adjacent a spinal column and vertebrae (also shown in phantom).

Also, this assembly can be held at an angle with the horizontal plane using the handle 108, with the semicircular cuts 103 and 111 resting against the outer curvature of the metal rods connecting the pedicle screws, as shown in FIG. 19.

Figure 20:
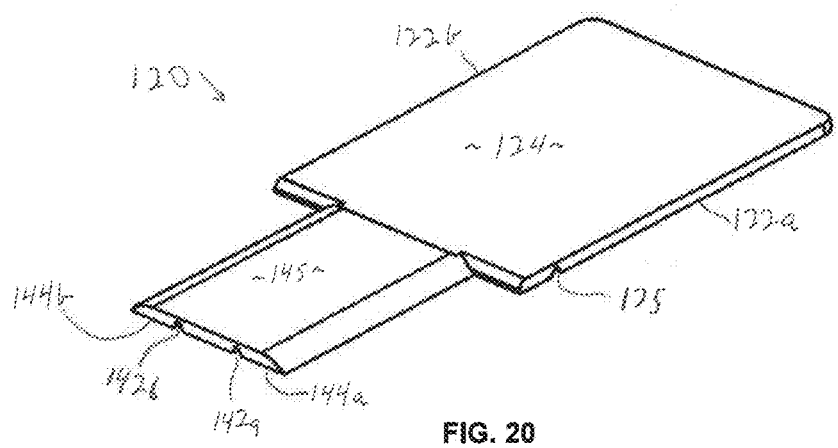
FIG. 20 is a perspective view of a top surface of a tray of a fifth embodiment of a BGM delivery device, shown in an unfolded state.
Figure 21:
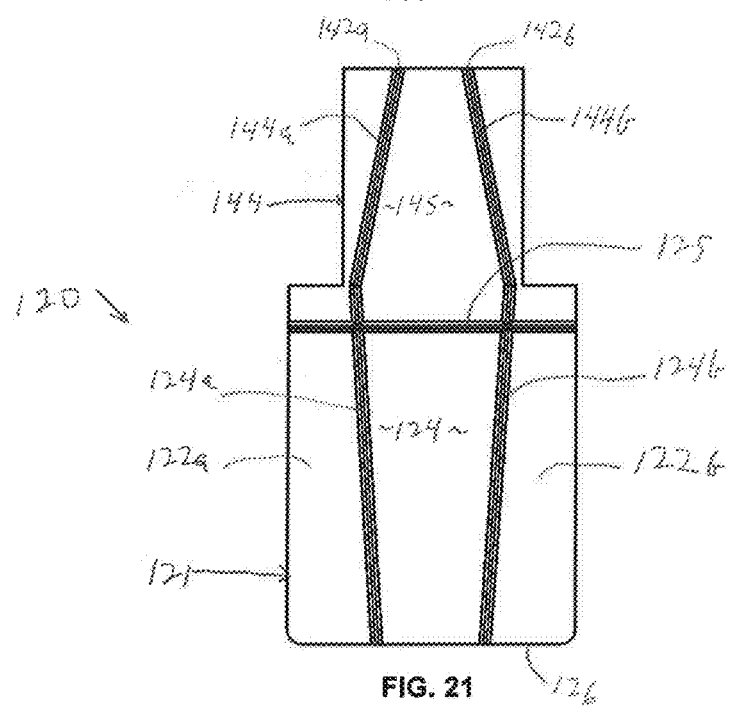
FIG. 21 is a bottom plan view of the bottom surface of the tray shown in FIG. 20, shown in an unfolded state.
Figure 22:
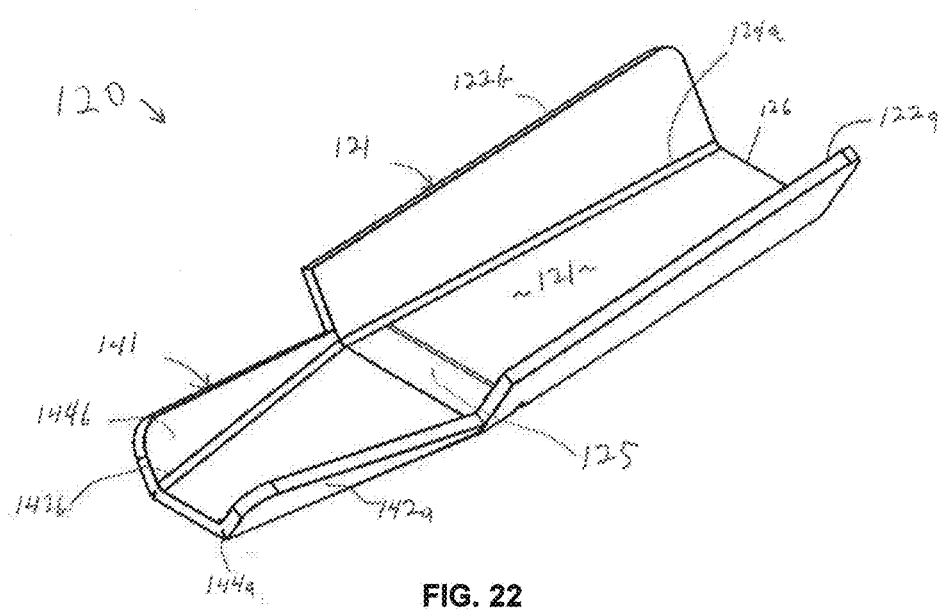
FIG. 22 is a perspective view of the tray shown in FIGS. 20 and 21, shown in a folded state.

FIGS. 20 through 22 illustrate a fifth embodiment of a unitary BGM delivery device 120 generally having a tray portion 121 and a handle portion 141.

FIG. 20 shows a top side of an unfolded device 120, and FIG. 21 shows a bottom side of the unfolded BGM device 120, while FIG. 22 show a perspective view of the unitary BGM device in a folded state, ready for use.

Referring now to the bottom side shown in FIG. 21, the tray portion 121 generally defines a platform portion 124 that can either have a generally rectangular shape, or as shown in the embodiment in FIGS. 20-23, can have a tapering design. The platform portion 124 is generally defined by opposing scored lines 124a and 124b that extend from a first end 125 which is adjacent to the handle portion 140, to a second end 126. When viewing the unitary BGM device 120 in its unfolded state, the score lines 124a, 124b, extend at acute angles from a line defined by the first end 125, such that the first end 125 has a larger width than the opposing second end 126. It is to be understood that while the embodiment of the platform portion 124 shown has a substantially planar surface, other embodiments of the platform portion 124 can have, for example, curved, frustoconical or other useful configurations.

The opposing score lines 124a, 124b define opposing arm portions 122a, 122b that extend beyond the tray portion 121 when in an unfolded state. When folded, as shown in FIG. 22, the arm portions 122a, 122b can have a shape that is tapering in height; for example, the arm portions 122 can have a first end 122a that is adjacent to the first end 125 of the platform portion 124. The first ends 122a of the arm portions 122 can have first heights that are less than second end portions 122b of the arm portions 122. In the embodiment shown in FIG. 20, the second end portions 122b of the arm portions 122 are adjacent to, and co-terminus with, the second end 126 of the platform portion 124.

Referring again to FIG. 21, the handle portion 141 can have a generally mirror image of the shape and dimensions to the tray portion 121. The handle portion 141 can either have a generally rectangular shape; or as shown in FIGS. 20-22 can have a tapering design. The handle portion 141 has a base 144 that is generally defined by opposing scored lines 144a and 144b that extend from a first end 145 which is adjacent to the tray portion 124, to a second end 146. When viewing the unitary device 120 in its unfolded state, the score lines 144a, 144b, extend at acute angles from a line defined by the first end 145, such that the first end 145 has a larger width than the opposing second end 146.

The opposing score lines 144a, 144b define opposing arm portions 142 that extend beyond the base 144. When folded, as shown in FIG. 22, the arm portions 142 can have a shape that is tapering in height; for example, the arm portions 142 can have a first end 142a that is adjacent to the first end 145 of the handle portion 141. The first ends 142a of the arm portions 142 can have first heights that are less than second end portions 142b of the arm portions 142. In the embodiment shown in FIGS. 20-22, the second end portions 142b of the arm portions 142 are adjacent to, and co-terminus with, the second end 146 of the handle portion 141.

During the spinal surgery, the mixing of BGM is performed on the tray portion 124. The tray portion 124 can be held at an angle with the horizontal plane using the rectangular handle during delivery of the BGM.

Using this folding state involving the score lines 124a, 124b, an opening that is to be proximal to the patient is defined by the distance between the opposing arm portions 122 of the tray portion 124. In certain embodiments, In the embodiment shown, the score lines 124a, 124, 144a, and/or 144b can be defined by sets of parallel extending fold lines, such that the distance (or width between opposing tray arm portions 122 and/or handle arm portions) can be varied, depending on which particular score line in the sets of score lines are used as a fold.

The principle and mode of operation of this invention have been explained and illustrated in its preferred embodiments. However, it must be understood that this invention may be practiced otherwise than as specifically explained and illustrated without departing from its spirit or scope.

What is claimed is:

1. A bone graft material delivery device comprising:
a tray comprising a first L-shaped arm formed by a sidewall and a base member, wherein the base member defines a platform, the platform comprising a first end at a proximal end of the device, a second end at a distal end of the device, an upper platform, and a lower platform parallel to the upper platform; and
a width adjustment member comprising a second L-shaped arm formed by a sidewall and a base member;
wherein the platform defines a slot that extends along a length of the platform from the first end to the second end between the upper platform and the lower platform, and the base member of the width adjustment member slides into the slot;
the platform being configured to provide a mixing and/or holding area for a bone graft material being delivered to a surgical site where an implant rod is being surgically inserted into a patient,
the tray being configured to substantially prevent bone graft materials from inadvertently being delivered to an unacceptable area of the surgical site;
wherein the first and second L-shaped arms define an opening between the respective sidewalls;
wherein at least one of the base members of the first and second L-shaped arms is tapered from the proximal end to the distal end with respect to the opening;
and wherein the upper platform and the lower platform are trapezoidal.

2. The bone graft material delivery device of claim 1, wherein the second end is positionable toward the implant rod, the second end having rounded cuts configured to be restingly positioned against the implant rod for stability during mixing and/or delivery of the bone graft material.

3. The bone graft material delivery device of claim 1, wherein the platform has a tapering design, such that the first end has a larger width than the second end.

4. The bone graft material delivery device of claim 1, wherein the width adjustment member includes at least one protrusion that slidably mates with a second slot in the platform such that the width of the bone graft material delivery device can be expanded laterally to fit different size fixations of the implant rod.

5. The bone graft material delivery device of claim 4, wherein the base member of the width adjustment member is configured to freely slide within the slot.

6. The bone graft material delivery device of claim 1, further comprising an upper lid assembly that pivotably mates with the second L-shaped arm.

7. The bone graft material delivery device of claim 6, wherein the lid assembly has a tapering design such that a first end of the lid assembly has a larger width than a second end of the lid assembly.

8. The bone graft material delivery device of claim 7, wherein the lid assembly comprises opposing first and second edges, wherein the second edge defines one or more hollow cylindrical shaped extrusions for receiving a pin-like member.

9. The bone graft material delivery device of claim 7, wherein the lid assembly and the second L-shaped arm form hinge joints that allow for opening and closing of the lid assembly.

10. The bone graft material delivery device of claim 1, wherein the second L-shaped arm comprises one or more hollow cylindrical shaped extrusions for receiving a pin-like member.

11. The bone graft material delivery device of claim 1, wherein the first L-shaped arm comprises a first cut adjacent to the second end at a bottom corner of the first L-shaped arm.

12. The bone graft material delivery device of claim 11, wherein the second L-shaped arm comprises a second cut at a corner thereof.

* * * * *